United States Patent [19]

Ryan

[11] 4,436,821

[45] Mar. 13, 1984

[54] SIMULATED HUMAN PLATELETS FROM RED BLOOD CELLS

[75] Inventor: Wayne L. Ryan, Omaha, Nebr.

[73] Assignee: Streck Laboratories, Inc., Omaha, Nebr.

[21] Appl. No.: 367,597

[22] Filed: Apr. 12, 1982

[51] Int. Cl.³ .................... G01N 33/48; C09K 3/00
[52] U.S. Cl. .................................. 436/10; 436/11; 435/2
[58] Field of Search .................. 436/10, 11; 435/2

[56] References Cited

U.S. PATENT DOCUMENTS

| | | | |
|---|---|---|---|
| 3,873,467 | 3/1975 | Hunt | 436/10 |
| 3,973,913 | 8/1976 | Louderback | 436/11 |
| 4,126,575 | 11/1978 | Louderback | 436/11 |
| 4,179,398 | 12/1979 | Hunt | 436/10 |
| 4,189,401 | 2/1980 | Louderback | 436/16 |
| 4,199,471 | 4/1980 | Louderback et al. | 436/17 |
| 4,264,470 | 4/1981 | Chastain, Jr. et al. | 436/10 |
| 4,279,775 | 7/1981 | Louderback et al. | 436/11 |
| 4,324,687 | 4/1982 | Louderback et al. | 436/10 |

*Primary Examiner*—Teddy S. Gron
*Attorney, Agent, or Firm*—Larson and Taylor

[57] ABSTRACT

A lysable, blood platelet reference control comprising a suspension of a mixture of permanently shrunken animal red blood cells in a suspension medium non-deleterious to said cells, said cells having been partially fixed with a fixing agent to reduce cell membrane elasticity prior to being shrunken, and said mixture of permanently shrunken cells in said suspension medium simulating in number, size and volume distribution the platelets present in human whole blood.

16 Claims, No Drawings

SIMULATED HUMAN PLATELETS FROM RED BLOOD CELLS

BACKGROUND OF THE INVENTION

1. Field of the Invention

This invention relates to a lysable blood platelet reference control for use in a number of routine hematologic determinations. More particularly, the invention is directed to lysable, blood platelet reference controls prepared from animal red blood cells.

2. State of the Art

Stabilized human platelets are commonly used as reference controls for checking the performance characteristics of blood particle counting instruments. The use of human platelets for this purpose, however, is not without its limitations. For example, human platelets are difficult to handle since they are easily activated and tend to aggregate. Human platelets are also very expensive.

Yet another shortcoming of stabilized human platelet reference controls has been experienced with multi-parameter reference controls which contain red blood cells and white blood cells as well as the platelets. In such multi-parameter reference controls, the red blood cells and the platelets mix at different rates, the red blood cells mixing more rapidly, and consequently, it is not uncommon to experience erratic platelet counts when the multi-parameter controls must be resuspended after days of settling.

It is not surprising, therefore, particularly with the advent of automated devices capable of performing multiple hemotogical determinations, to find a growing need for less expensive substitutes useful as blood platelet reference controls. U.S. Pat. No. 4,179,398 to Robert A. Hunt describes a blood platelet reference control prepared by shrinking goat red blood cells to the size of human blood platelets and then fixing the shrunken goat blood cells to stabilize them. The shortcoming of the platelet control composition of U.S. Pat. No. 4,179,398 is that the cells shrunken by a hypertonic solution as described in the patent tend to return to their original shape. In other words, simulated platelets prepared by U.S. Pat. No. 4,179,398 when put into an isotonic solution often return to their original shape thereby resulting in an inaccurate count.

Another drawback of the platelet control composition of U.S. Pat. No. 4,179,398 resides in the fact the size of the simulated platelets prepared is only the general size of human blood platelets and not the size distribution of human blood platelets. Any system for automated platelet counting which distinguishes human platelets from other cells in the blood on the basis of the characteristic size range and volume distribution of platelets requires that the reference control material closely simulate the size range and volume distribution characteristics of platelets in normal human blood.

U.S. Pat. No. 4,264,470 to Chastain, Jr. et al recognizes the problem associated with reference controls of the type aforementioned which do not closely simulate the size range and volume distribution characteristics of platelets in normal human blood and proposes a method for obtaining goat blood cells with the desired size and volume distributions by using different goats, inducing anemia in goats, etc., determining the number and size distribution of the red blood cells in the various samples thus obtained and then blending the red blood cells to gain the appropriate size and volume distributions. The multiple steps and controls necessary to such a prior art process renders it unduly difficult and cumbersome.

Another disadvantage in prior art reference controls for use in blood platelet controls resides in the fact that they are "fixed" or stabilized. When "fixed" platelets are used in multi-parameter controls containing red blood cells, white blood cells and platelets, the platelets may add to the white cell count because "fixed" platelets do not lyse or fragment. Consequently, when a white blood cell count is taken some of the large platelets are counted in the white blood cell channels giving an inaccurate total white blood cell count.

OBJECTS OF THE INVENTION

Accordingly, it is an object of the invention to provide an inexpensive, lysable platelet substitute useful in multi-parameter reference controls.

Another object of the invention is to provide a method of conveniently preparing from the red blood cells of animals a reference control material that closely simulates the size range and volume distribution characteristics of platelets in normal human blood.

A further object of the invention is to prepare a lysable, permanently shrunk red blood cell suitable for use as a platelet reference control which does not return to its original shape when placed in an isotonic solution.

Yet a further object of the invention is to provide simulated platelets as reference controls which mix at approximately the same rate as red blood cells thereby eliminating or minimizing the chance of erratic platelet counts when used together with red blood cells and white blood cells in multi-parameter controls.

SUMMARY OF THE INVENTION

These and other objects of the invention are obtained by a lysable blood platelet reference control comprising a suspension of a mixture of permanently shrunken animal red blood cells in a suspension medium non-deleterious to said cells, said cells having been partially fixed with a fixing agent to reduce cell membrane elasticity prior to being shrunken, and said mixture of permanently shrunken cells in said suspension medium simulating in number, size and volume distribution the platelets present in human whole blood.

The lysable, blood platelet reference controls of the invention are prepared by treating animal red blood cells larger than or within the size range of human blood platelets, with a fixing agent for red blood cells for a time sufficient to partially rigidify the membrane of red blood cells to a state enabling subsequent shrinking of said cells to a permanently shrunken condition, subjecting distinct groups of said partially fixed red blood cells to different osmotic pressures to permanently shrink the cells to different sizes, said groups and pressures being selected so as to provide on shrinking a mixture of permanently shrunken cells that simulate in number, size and volume distribution the platelets present in human whole blood.

One preferred method of preparing a lysable, blood platelet reference control comprises contacting animal red blood cells larger than or within the size range of human blood platelets with a fixing agent for red blood cells for a time sufficient to partially rigidify the red blood cell membrane to a state enabling shrinking of said cells to a permanently shrunk condition, subjecting one group of said partially fixed cells to a hypertonic solution of 20 to 40% v/v, preferably about 30% alkylene glycol of 1 to 4 carbon atoms, a second group of said partially fixed cells to a hypertonic solution of 40 to 60% v/v, preferably about 50% v/v alkylene glycol of 1 to 4 carbon atoms and a third group of said partially fixed cells to an aqueous solution of 60 to 80% v/v, preferably about 70% v/v alkylene glycol of 1 to 4 carbon atoms, mixing the resulting shrunken cells to provide a mixture of permanently shrunken cells that simulate in number, size and volume distribution the platelets present in human whole blood.

Another preferred method for preparing the lysable, blood platelet reference control of the invention involves adding a dispersion of fixed cells partially fixing as noted above over 100% alkylene glycol of 1 to 4 carbons so as to form a layer thereover, allowing a concentration gradient to develop between the alkylene glycol and said dispersion of cells, said concentration gradient permitting production upon shrinking of said cells permanently shrunken cells that simulate in number, size and volume distribution platelets present in whole human blood and maintaining said concentration gradient for a time sufficient to provide a mixture of said permanently shrunken cells.

DETAILED DESCRIPTION OF THE INVENTION

The red blood cells from which the lysable platelet reference controls of the present invention are prepared can be suitable animal red blood cells. It is only necessary that the starting red blood cells from the animal species be larger in size or within the size range of the human blood platelets (approximately 2–40$u^3$) and shrinking the cells to a point where they fall within the approximate size of the platelets of human blood. Thus, there is no need for a particular species of red blood cell. In general, however, the starting red blood cells will have a mean cell volume of about 25 to 55$u^3$. Illustrative of suitable red blood cells are those from the blood of goats, sheep, pigs, cows, cats and the like.

Pursuant to the method of the present invention, whole blood from a donor animal is collected and mixed with an anticoagulant and the plasma and red blood cells are separated from the blood by any of the conventional methods such as centrifugation or settling. The anticoagulant may be sodium citrate, ammonium oxalate, potassium oxalate, or any other conventional anticoagulant which will not have an adverse effect on the red blood cells. The separated red blood cells are then washed free of all plasma, anticoagulant and other blood particles and suspended in a suspension medium nondeleterious to the red blood cells. The suspension medium is preferably a physiological salt solution such as an isotonic saline solution advantageously buffered to a pH neutral to alkaline, preferably a pH of 7 to 9. Preferred buffering agents include the alkali metal phosphates such as disodium phosphate, monopotassium phosphate, monosodium phosphate, sodium bicarbonate and the like and mixtures thereof. In general, suspensions of up to 50% by volume, preferably about 10 to 30% by volume red blood cells are prepared.

Next the elasticity of the red cell membrane is decreased, that is, the red cell membrane is partially rigidified by treating the red blood cells in suspension with a fixing agent. Fixing agents for red blood cells are well known to those of ordinary skill in the art and include, for instance, aldehydes, such as formaldehyde and glutaraldehyde, tannic acid or other chemical fixative agents. The amount of fixing agent added to the suspension of red blood cells will vary depending upon the particular species of red blood cells employed, the number of cells in the suspension being treated, and the fixing agent employed. In the case of aldehyde fixing agents, the concentration will usually vary from 0.004 to 0.10% by weight per $1 \times 10^6/mm^3$ of red blood cells. With glutaraldehyde and sheep red blood cells a concentration of glutaraldehyde about 0.01 to 0.02% per $10^6$ cells is preferred. When goat red blood cells are used a concentration of about 0.004 to 0.015% glutaraldehyde per $10^6$ cells is preferred.

In all cases the reaction of the fixing agent with the red blood cells is allowed to proceed until they are partially rigidified. By the term "partially rigidified" as used herein and in the appended claims is meant a degree of rigidification that enables subsequent shrinking of the red blood cells to a permanently shrunk condition. Usually this degree of rigidification falls in the range of 40 to 80% of complete rigidification for the red blood cells employed. Ordinarily the fixing period necessary to achieve the desired degree of rigidification comprises about 24 to 48 hours.

After the red blood cells have been partially rigidified, suspension thereof are divided into a plurality of distinct groups or lots and each group is subjected to a different osmotic pressure to shrink the red blood cells in each suspension. Since different osmotic pressures are applied to the groups, the family of red cells in each will be of a different size. The osmotic environments which will exert the osmotic pressure necessary to shrink the red blood cells are well known to those of ordinary skill in the art. Generally, hypertonic solutions are the commonly used environments for generating the desired osmotic pressure but any of the others can be employed as well. The preferred hypertonic solutions are aqueous solutions of alkylene glycols having 1 to 4 carbon atoms such as ethylene glycol, propylene glycol and butylene glycol. Of these, ethylene glycol is preferred. The different osmotic pressure applied to the distinct groups of red blood cell suspension can be generated by varying the concentrations of alkylene glycol employed in the shrinking step. This can be achieved by adding alkylene glycol to each suspension of partially rigidified red blood cells until the desired concentration of alkylene glycol is reached. The highest concentration of alkylene glycol produces the smallest particles. It is important to appreciate that the osmotic shock or pressure delivered to the partially rigidified red cells must not be done too gradually or the membrane does not collapse adequately. If the osmotic pressure or shock administered is too great, a population of small "platelets" is produced. On the other hand, if the osmotic shock is too small, overly large "platelets" are produced. It has been found that in most cases the addition of the alkylene glycol to three lots in suspension of partially rigidified red cells to final concentrations of approximately 30%, 50% and 70%, respectively, provides upon shrinking, sizes of red blood cells which upon blending produce a log normal distribution curve corresponding to that of human platelets.

In the shrinking step, the red cells start to collapse shortly after the addition of the alkylene glycol and the shrinking is monitored as by periodically scanning the cells with a cell analyzing instrument such as a Coulter ZBI Channelyzer to determine the size to which the cells have shrunk. When the desired size is attained in each lot, the shrinking is stopped by the addition of sufficient volumes of suspension medium such as saline to decrease the osmolarity. Once the red cells are shrunk pursuant to the method of the invention, the cells remain permanently shrunken and do not return to their original shape when put into a isotonic solution.

After the shrinking process is finished, the permanently shrunk cells are separated from the suspension mediums as by centrifugation and washed preferably with a buffered saline to remove the alkylene glycol. The groups or lots of washed and shrunk red blood cells are then blended to produce a mixture of permanently shrunken cells that simulate in number, size and volume distribution the platelets in human whole blood.

In an alternative method of preparing the reference controls of the present invention, partially rigidified animal red blood cells prepared in a buffered suspension as described above are layered over 100% alkylene glycol of 1 to 4 carbon atoms, preferably ethylene glycol. A concentration gradient soon develops between the alkylene glycol and the buffered suspension or dispersion containing the red blood cells. The concentration gradient established pursuant to this embodiment is one in which there will be produced shrunken red blood cells that simulate in number, size volume distribution of the platelets present in whole human blood. Since the highest concentration of alkylene glycol in the gradient effects the greatest amount of shrinkage and the lowest concentration which provides the desired number, size and volume distribution of shrunken red blood cells can be provided by the appropriate selection of the depths of the alkylene glycol layer and the suspension of an adequate number of partially rigidified red blood cells. In all instances however, the concentration gradient is maintained for a time sufficient to effect the desired shrinkage and this time can be monitored by a periodic scanning of the cells at various locations in the concentration gradient with a cell analyzing instrument as aforementioned. In most instances, the shrinkage time will be about 24 to 48 hours.

When the shrinkage is complete the permanently shrunk red blood cells are separated and washed to provide red blood cells in number and size distribution that simulate that of human whole blood platelets. Thus, in this method no blending step is necessary and the washed red blood cells need only be added to a non-deleterious suspension medium such as buffered saline or other suitable non-plasma type fluids.

The reference control compositions of the invention may also include other addenda conventionally added to such compositions. Illustrations of additives that can be included are bactericidal agents such as sodium azide and sodium merthiolate, antiseptics such as phenol; stabilizing agents such as osmium textroxide; metabolic preservatives such as the purines and pyrimidines; dispersing agents such as gelatin, dialkali metal salts of naphthol-sulfonic acids, dextran and the like.

The following examples are given by way of illustration and are not to be construed as limiting the invention, many variations of which are possible without departing from the spirit or scope thereof.

EXAMPLE I

Sheep blood is collected in a citrate anticoagulant and the blood is centrifuged to remove the plasma. The red cells are washed with isotonic phosphate buffered saline to remove all plasma and anticoagulant.

The sheep cells are counted and the concentration of red cells adjusted to $1 \times 10^6/mm^3$ by addition of phosphate buffered saline having a pH of 7.4. glutaraldehyde (25%) is then slowly added to the red cells with mixing until a final concentration of 0.016% glutaraldehyde is provided. The reaction is allowed to proceed overnight at 6° C. The next day the resulting partially rigidified red blood cells are divided into three lots and ethylene glycol is added to each lot to produce final concentrations of 30%, 50%, and 70% v/v ethylene glycol, respectively. The red cells start shrinking after addition of the ethylene glycol. At intervals of one hour, the cells are scanned to determine the size in a Coulter ZBI Channelyzer. Once the approximate size is obtained, the reaction is stopped by the addition of three volumes of phosphate buffered saline to decrease the osmolarity. After the shrinking process is completed, the cells are centrifuged and washed three times in phosphate buffered saline to remove the ethylene glycol.

One volume of each of the three lots are then blended to produce a log normal curve resembling human platelets.

EXAMPLE II

Sheep blood is collected in citrate anticoagulant. The blood is centrifuged to separate the red cells and plasma. The cells are washed with isotonic phosphate buffered saline to remove all plasma. The sheep cells are counted and the concentration of red cells adjusted to $1 \times 10^6/mm^3$ by addition of phosphate buffered saline having a pH of 7.4. Glutaraldehyde (25%) is added dropwise to the red cells with continuous mixing until a final concentration of 0.016% glutaraldehyde is attained. The cells are placed at 6° C. for 24 hours. After 24 hours the reaction is complete and cells are partially rigidified. 100 ml of the cells are placed in a glass cylinder 8 cm in diameter—100 ml of ethylene glycol is layered into the bottom of the cylinder by adding through a glass tube positioned on the bottom of the cylinder. The cells and ethylene glycol are left at 25° for 72 hours to establish the appropriate concentration gradient. This method produces a log normal distribution of red cells which closely resemble the distribution of human platelets.

It is claimed:

1. A lysable, blood platelet reference control comprising a suspension of a mixture of permanently shrunken animal red blood cells in a suspension medium non-deleterious to said cells, said cells having been partially fixed with a fixing agent to reduce cell membrane elasticity prior to being shrunken, and said mixture of permanently shrunken lysable cells in said suspension medium simulating in number, size and volume distribution the platelets present in human whole blood.

2. A lysable, platelet reference control according to claim 1 wherein the shrunken animal red blood cells are sheep blood cells.

3. A lysable, platelet reference control according to claim 1 wherein the suspension medium is saline solution.

4. A lysable, platelet reference control according to claim 1 wherein the fixing agent is an aldehyde.

5. A lysable, platelet reference control according to claim 3 wherein the saline solution is a phosphate buffered saline solution.

6. A lysable, platelet reference control according to claim 4 wherein the aldehyde is glutaraldehyde.

7. A method of preparing a lysable, blood platelet reference control comprising treating animal red blood cells larger than or within the size range of human blood platelets with a fixing agent for red blood cells for a time sufficient to partially rigidify the red blood cell membrane to a state enabling shrinking to a permanently shrunk condition, subjecting distinct groups of said partially fixed red blood cells to different osmotic pressures to permanently shrink the cells to different sizes, said groups and pressure being selected so as to provide on shrinking a mixture of permanently shrunken lysable cells that simulate in number, size and volume distribution the platelets present in human whole blood.

8. A method according to claim 7 wherein the fixing agent is aldehyde.

9. A method according to claim 8 wherein the aldehyde is glutaraldehyde.

10. A method according to claim 7 wherein the osmotic pressure is induced by contacting the partially fixed red blood cells with a hypertonic solution of ethylene glycol.

11. A method according to claim 7 wherein the fixing agent is glutaraldehyde and the osmotic pressure is induced by contacting the partially fixed red blood cells with a hypertonic solution.

12. A method according to claim 11 wherein the hypertonic solution is a hypertonic solution of ethylene glycol.

13. A method of preparing a lysable, blood platelet reference control comprising treated animal red blood cells larger than or within the size range of human blood platelets with a fixing agent for red blood cells for a time sufficient to partially rigidify the red blood cell membrane to a state enabling shrinking of said cells to a permanently shrunk condition, subjecting one group of said partially fixed cells to a hypertonic solution of 30% w/w alkylene glycol of 1 to 4 carbon atoms, a second group of said partially fixed cells to a hypertonic solution of 50% w/w alkylene glycol of 1 to 4 carbon atoms and a third group of said partially fixed cells to an hypertonic solution of 70% w/w alkylene glycol of 1 to 4 carbon atoms, mixing the resulting shrunk cells to provide a mixture of permanently shrunken lysable cells that simulate in number, size and volume distribution the platelets present in human whole blood.

14. A method according to claim 13 wherein the animal cells are sheep cells.

15. A method according to claim 13 wherein the alkylene glycol is ethylene glycol.

16. A method of preparing a lysable, blood platelet reference control comprising treating animal red blood cells larger than or within the size range of human blood platelets with a fixing agent for red blood cells for a time sufficient to partially rigidify the red blood cell membrane to a state enabling shrinking of said cells to a permanently shrunk condition, adding the resulting dispersion of partially fixed cells over 100% ethylene glycol so as to form a layer thereover, allowing a concentration gradient to develop between the ethylene glycol and said dispersion of cells, said concentration gradient permitting the production upon shrinking of said cells, maintaining said concentration gradient for a time sufficient to provide a mixture of permanently shrunken lysable cells that simulate in number, size and volume distribution the platelets present in whole blood.

* * * * *